(12) United States Patent
Kheradmandnia

(10) Patent No.: US 9,351,805 B2
(45) Date of Patent: May 31, 2016

(54) IN-SITU TOOTH FILLING SYSTEM AND METHOD UTILIZING EXTERNAL CURING STEP

(71) Applicant: Hamid Kheradmandnia, San Diego, CA (US)

(72) Inventor: Hamid Kheradmandnia, San Diego, CA (US)

(*) Notice: Subject to any disclaimer, the term of this patent is extended or adjusted under 35 U.S.C. 154(b) by 18 days.

(21) Appl. No.: 13/750,612

(22) Filed: Jan. 25, 2013

(65) Prior Publication Data

US 2014/0212835 A1 Jul. 31, 2014

(51) Int. Cl.
*A61C 5/00* (2006.01)
*A61C 5/04* (2006.01)
*A61C 5/06* (2006.01)
*A61C 13/15* (2006.01)

(52) U.S. Cl.
CPC . *A61C 5/04* (2013.01); *A61C 5/062* (2013.01); *A61C 19/004* (2013.01)

(58) Field of Classification Search
CPC ......... A61C 5/04; A61C 5/062; A61C 19/004
USPC ............................... 433/215, 225–226, 228.1
See application file for complete search history.

(56) References Cited

U.S. PATENT DOCUMENTS

| 4,362,508 A * | 12/1982 | Soderstrom | A61C 5/04 433/220 |
| 4,726,770 A * | 2/1988 | Kurer | A61C 5/00 433/215 |
| 5,284,443 A * | 2/1994 | Weil | A61C 5/04 433/221 |
| 6,168,431 B1 * | 1/2001 | Narusawa | A61C 5/00 433/226 |
| 2002/0115042 A1 * | 8/2002 | Hasel | A61C 5/00 433/228.1 |
| 2003/0148247 A1 * | 8/2003 | Sicurelli, Jr. | A61C 13/30 433/220 |

* cited by examiner

*Primary Examiner* — Matthew Nelson
(74) *Attorney, Agent, or Firm* — Steins & Associates, P.C.

(57) ABSTRACT

An In-situ Tooth Filling System and Method Utilizing External Curing Step. The method and system utilizes the heat-/light-/vacuum-curing process normally available only in a dental laboratory. Like the conventional dental prosthetic production process, the filling is attached to the tooth void utilizing curable cement. Unlike the conventional (indirect) method, however, the instant method is completed totally within a single appointment in the dentist's office. The system utilizes fill stems that are made from curable filling material. These stems will become a part of the filling when the filling is cured. The filling is partially cured and then removed from the tooth for final curing in a vacuum oven that heat- and/or light-cures the filling.

15 Claims, 6 Drawing Sheets

IN-SITU TOOTH FILLING SYSTEM AND METHOD UTILIZING EXTERNAL CURING STEP

This application is filed within one year of, and claims priority to Provisional Application Ser. No. 61/686,005, filed Mar. 29, 2012.

BACKGROUND OF THE INVENTION

1. Field of the Invention

This invention relates generally to dental processes and systems and, more specifically, to an In-situ Tooth Filling System and Method Utilizing External Curing Step.

2. Description of Related Art

Conventional tooth repair approaches can typically be grouped into two categories: (1) those conducted in the dentist's office in a single visit (e.g. fillings), and (2) those requiring an intermediate step conducted at a dental lab (e.g. dental prosthetics). As depicted in FIG. 1, the typical in-situ filling method 10 proceeds through the following steps: the tooth having the cavity is first drilled out to create a clean void that is suitable for filling 100. The dentist then injects a filling material (composite, metal or other) into the void previously created in the tooth 102. For fillings made from composite, the material must be cured once it has been injected so that it is hard enough to function as a repair for the tooth. The injection and curing of the composite material is typically done in layered steps 104. Generally a light-reactive filling material is used, with ultraviolet wavelength being the most common. Once filled and cured, the dentist shapes and polishes the filling 106 so that the patient has a comfortable bite and no sharp or rough edges. Rosenfeld, U.S. Pat. No. 7,189,076 discusses a typical layered filling and curing method for in-situ tooth filling.

The in-situ filling method is by far the most prevalent approach used to repair a person's tooth because it is completed in a single office visit, and because it therefore tends to be the lowest-cost method available. In-situ tooth fillings are commonly covered by dental insurance. The problems with the in-situ filling method are related to durability and comfort. Because the composite material used to fill the tooth is cured while in the tooth, the dentist cannot use the type of composite material that is heat-cured in an oven, or make sure that the composite material used is totally cured and hardened. The heat-curable/light-curable composite material is used to create one of the hardest and most durable finished dental prosthetics available. Furthermore, during in-situ filling there will be air bubbles and gaps between the filling and the walls of the void created in the tooth during the filling process. These gaps are the result of the slight shrinkage that occurs during the curing process. Any gaps between the filling and the tooth will result in tooth discomfort for the patient and a potential for bacterial impregnation (which further reduces the fillings lifespan).

In cases where filling the tooth in the dentist's office is either not desirable, or it is not feasible, a prosthetic filling (or tooth) is installed. FIG. 2 depicts the steps employed in a conventional dental prosthetic installation method 12.

First, an impression of the undisturbed tooth is made 108. Next, 100, the tooth is prepared for filling by drilling a clean void in the tooth. A second impression is then made 110; this impression is of the tooth after the void has been drilled. For now, these are the final steps conducted in the dentist's office during this visit (although a temporary filling will usually be installed to prevent undue discomfort for the patient and to keep the void clean).

At the dental prosthetics lab, the first and second impressions are used to make a single prosthetic shaped to fit perfectly into the void created in the patient's tooth 112. This prosthetic piece is then cured by heat (and sometimes partially by light) while being held in a vacuum state at the dental lab 114.

At a second appointment at the dentist's office, the prosthetic is installed into the void previously formed in the patient's tooth, and is held in place by specialized adhesive cement 116. Any shrinkage of the prosthetic that occurred during curing is compensated for by the dental adhesive used to permanently bond the prosthetic to the patient's tooth. The result is a perfectly-fitted repair area that is much less likely to cause the patient future discomfort or to suffer from a short lifespan. Examples of these conventional approaches are discussed in Hewell, U.S. Pat. No. 4,695,254, Rubbert (I), U.S. Pat. No. 7,708,557 and Rubbert (II), U.S. Patent Application Publication No. US12/0064489.

While prosthetic filling methods produce a very high quality result for the patient, they tend to be quite expensive and time-consuming. As a result, they are only chosen infrequently for tooth repair. What is needed is a tooth repair method and system that provides the comfort and durability of a dental prosthetic with the cost and convenience of an in-situ installed filling.

SUMMARY OF THE INVENTION

In light of the aforementioned problems associated with the prior devices and methods, it is an object of the present invention to provide an In-situ Tooth Filling System and Method Utilizing External Curing Step. The method and system should utilize the heat/light-/vacuum-curing process normally available only in a dental implant laboratory. Like the conventional dental implant production process, the filling should be attached to the tooth void utilizing curable cement. Unlike the implant method, however, the instant method should be completed totally within a single appointment in the dentist's office. The system should utilize fill stems that are made from curable filling material. These stems should become a part of the filling when the filling is cured. The filling should be partially cured and then removed from the tooth for final curing in a vacuum oven that heat- and/or light-cures the filling.

BRIEF DESCRIPTION OF THE DRAWINGS

The objects and features of the present invention, which are believed to be novel, are set forth with particularity in the appended claims. The present invention, both as to its organization and manner of operation, together with further objects and advantages, may best be understood by reference to the following description, taken in connection with the accompanying drawings, of which:

DETAILED DESCRIPTION OF THE PREFERRED EMBODIMENTS

The following description is provided to enable any person skilled in the art to make and use the invention and sets forth the best modes contemplated by the inventor of carrying out his invention. Various modifications, however, will remain readily apparent to those skilled in the art, since the generic principles of the present invention have been defined herein specifically to provide an In-situ Tooth Filling System and Method Utilizing External Curing Step.

Figure 1:
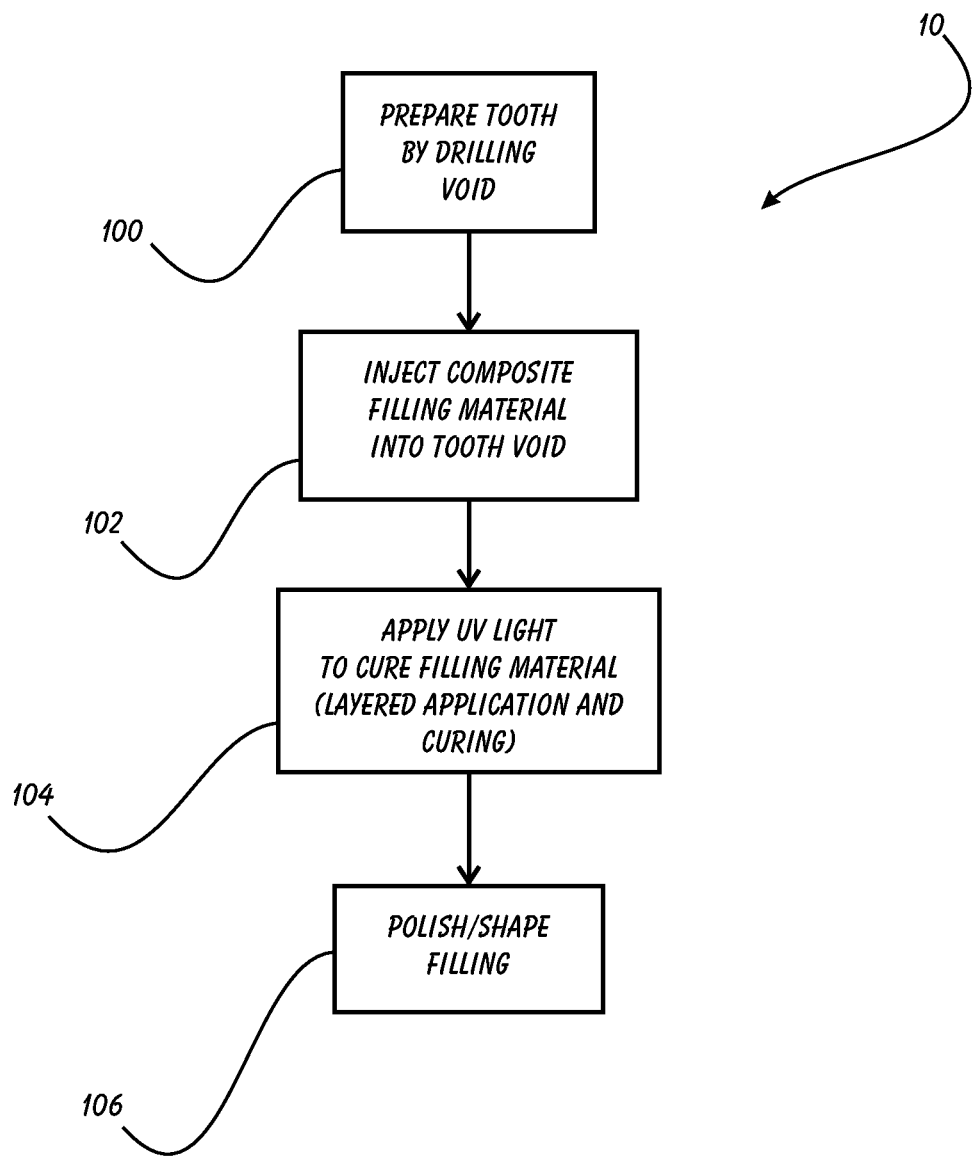
FIG. 1 is a flowchart depicting the steps of the conventional method for filling a tooth in a patient's mouth.
Figure 2:
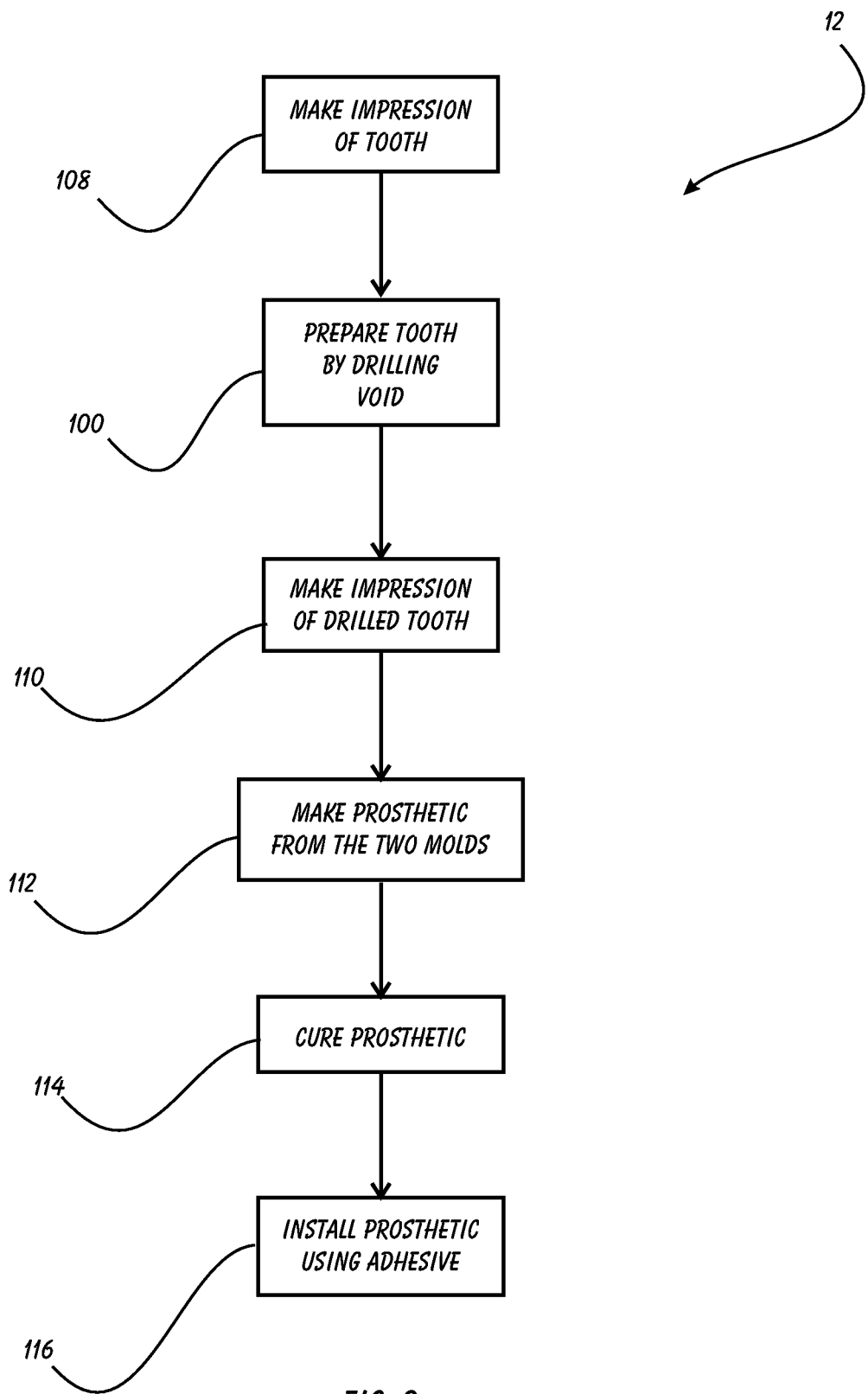
FIG. 2 is a flowchart depicting the steps of the conventional method for creating a dental prosthetic.
Figure 3:
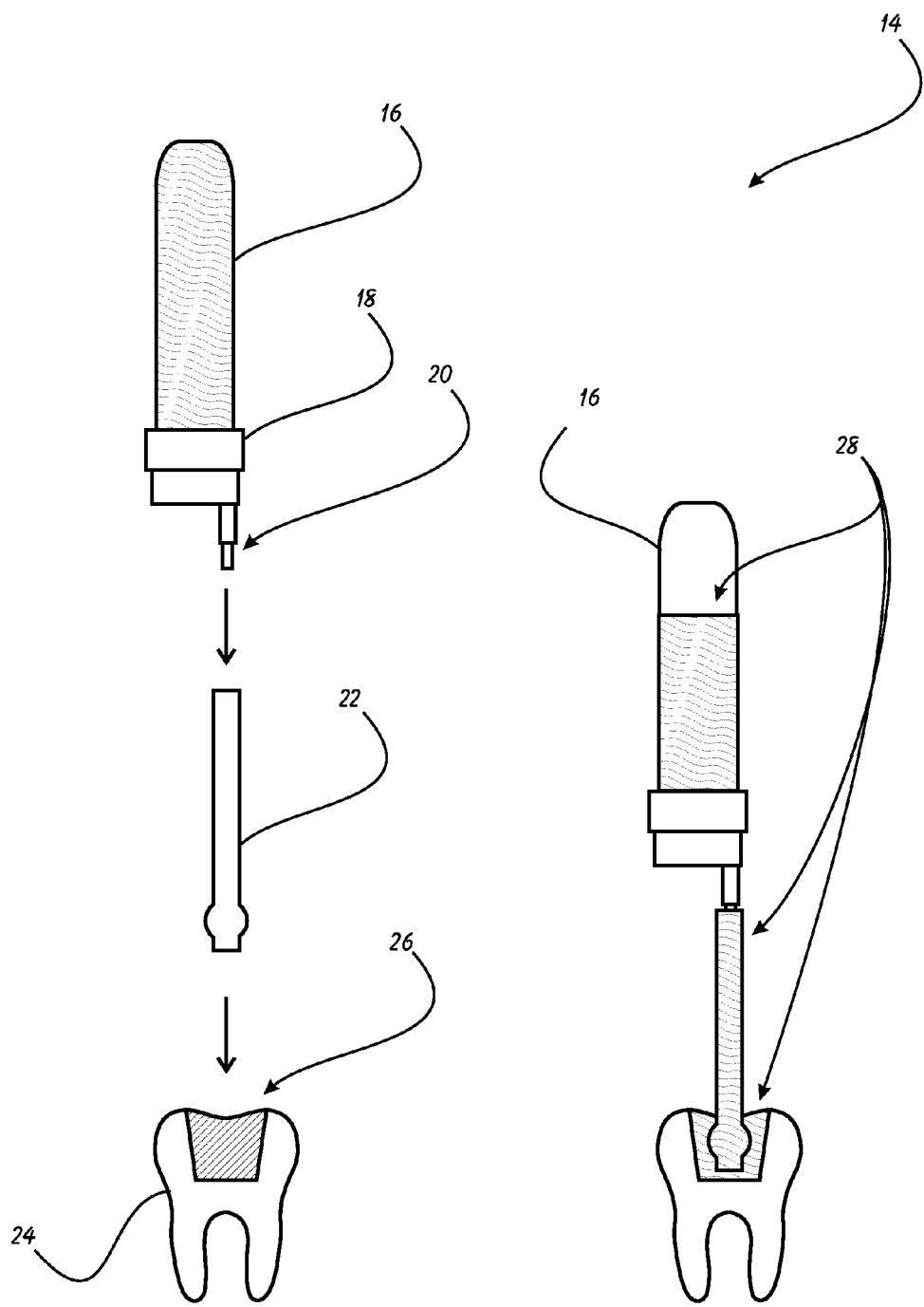
FIG. 3 depicts an example of the elements involved in the implementation of the method of the present invention.

The present invention can best be understood by initial consideration of FIG. 3.[1] FIG. 3 depicts an example of the elements involved in the implementation of the method of the present invention (further detail is provided herein below in connection with other drawing figures). A conventional method of dispensing liquid filling material for the purpose of creating dental fillings and prosthetics is via the device 15 depicted in FIG. 3. The dispenser 15 has a reservoir 16 filled with filling material 28 and capped by a head 18. The head 18 is formed with a tubular nozzle 20 protruding from one end.

[1] As used throughout this disclosure, element numbers enclosed in square brackets [ ] indicates that the referenced element is not shown in the instant drawing figure, but rather is displayed elsewhere in another drawing figure.

The dentist positions the tip of a tubular sacrificial stem 22 inside of a void 26 formed in the tooth 24. The stem 22 is preferably made from the same or similar material as the filling material 28, but it has been at least partially cured so that it is somewhat hardened. The stem 22 may still be pliable, but the material is cured enough so that it can be used to dispense the liquid filling material 28, and then utilized as a handle later on in the process.

The nozzle 20 (outside of the patient's mouth) is positioned in the opposing end of the stem 22 (the nozzle 20 attaches to the stem 22 with a click), and the filling material 28 is extruded out through the nozzle 20 so that it travels down the stem 22 and fills the void 26. It is not critical that the top surface of the tooth 24 is in a finished state, since the top of the filling material (in the filled void 26) will be shaped an polished during a later step in the filling process of the present invention. Now turning to FIG. 4, we will examine this novel process in detail.

Figure 4:
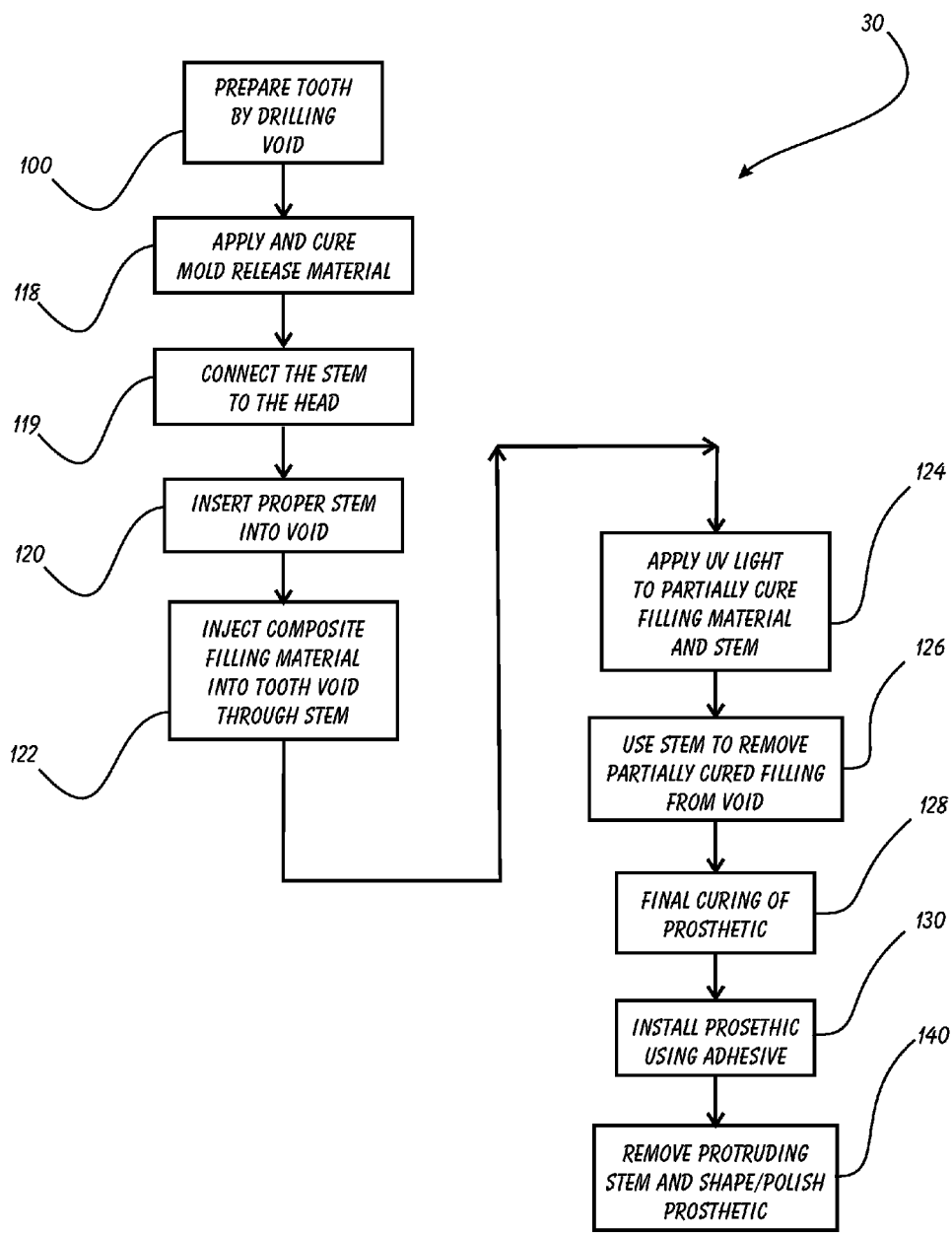
FIG. 4 is a flowchart depicting the steps of a preferred embodiment of the in-situ filling method.

FIG. 4 is a flowchart depicting the steps of a preferred embodiment of the in-situ filling method 30. As with the prior in-situ filling method, the first step is to prepare the tooth by drilling the proper void 100 into which the filling material will be place. Next, a conventional mold release material is applied into the void 118, and cured if necessary (usually by application of UV or other light). The mold release material is designed to allow for cured (or semi-cured) filling material to be more easily removed from a mold. In this case, the mold release material is applied into the tooth void itself.

Figure 6:
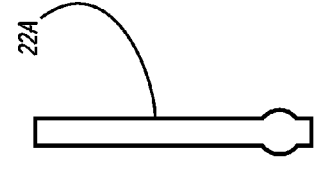
FIG. 6 depicts a series of preferred stem elements used in the method of FIGS. 3-5.
Figure 6:
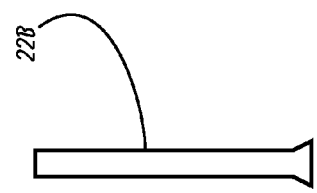
Figure 6:
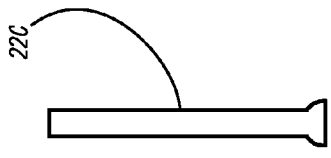
Figure 6:
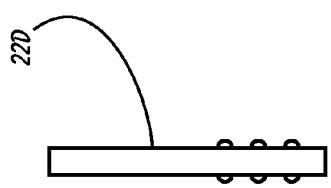
Figure 6:
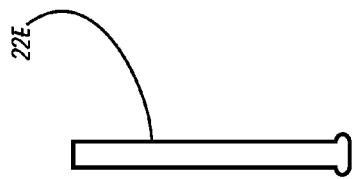
Figure 6:
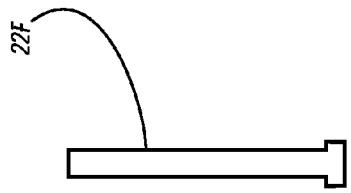
Figure 6:
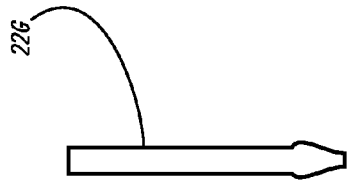
Figure 6:
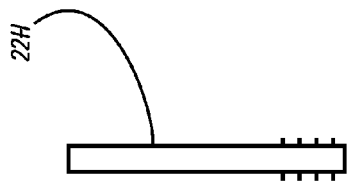
Figure 6:
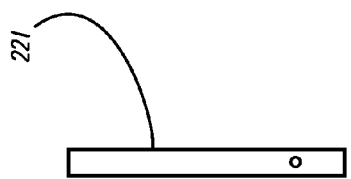

A stem is first attached to the end of the head 119. The stem is then inserted into the void 120 (after being attached to the nozzle 20). The shape of the stem may vary so that it fits well into the void. Some examples of the possible shapes and features of the various stems are depicted below in FIG. 6. As discussed above, the stem is preferably formed from cured filling material, and is basically an elongate tube.

Non-hardened composite filling material is then injected through the stem and into the tooth void until the void is completely filled 122. It should be noted that up to this point, no impression or mold has been made of the tooth (i.e. unlike the prior art dental appliance method discussed previously). Ultraviolet or other specialized light is applied to the void and stem (which is also filled with filling material) until it is partially cured 124. Typically only a single fill and cure step will be conducted, since there will be a full curing step later on in the process.

Once the filled void has been partially cured (by light only), the entire assembly of the stem and filled void will be a single, hardened piece of filling material. It is then a simple matter of pulling on the stem (after the nozzle has been removed) until the partially cured filling assembly is released from the void 126. This partially cured prosthetic/filling assembly is then placed into a specialized oven in order to bake the assembly until it is fully heat- and light-cured 128 while under vacuum. This heat-/light-curing step will cause the prosthetic/filling assembly to become just as hard as a conventional lab-prepared prosthetic. The difference is that by following the process described here, it can be done in the dentist's office in a single patient visit, while the patient waits. Furthermore, if the prosthetic/filling assembly experiences shrinkage, all of that shrinkage will have occurred by the time that the assembly is removed from the oven and cooled down.

Once the prosthetic/filling assembly has cooled and trimmed, it can be re-inserted into the tooth void. First, a suitable bonding agent or adhesive is applied to the tooth void and/or the prosthetic/filling assembly, and then the prosthetic/filling is re-inserted into the void 130. The bonding agent/cement will fill any gaps between the outside of the prosthetic/filling and the walls of the void, while also creating a virtually permanent bond between the prosthetic/filling assembly and the tooth.

Figure 5:
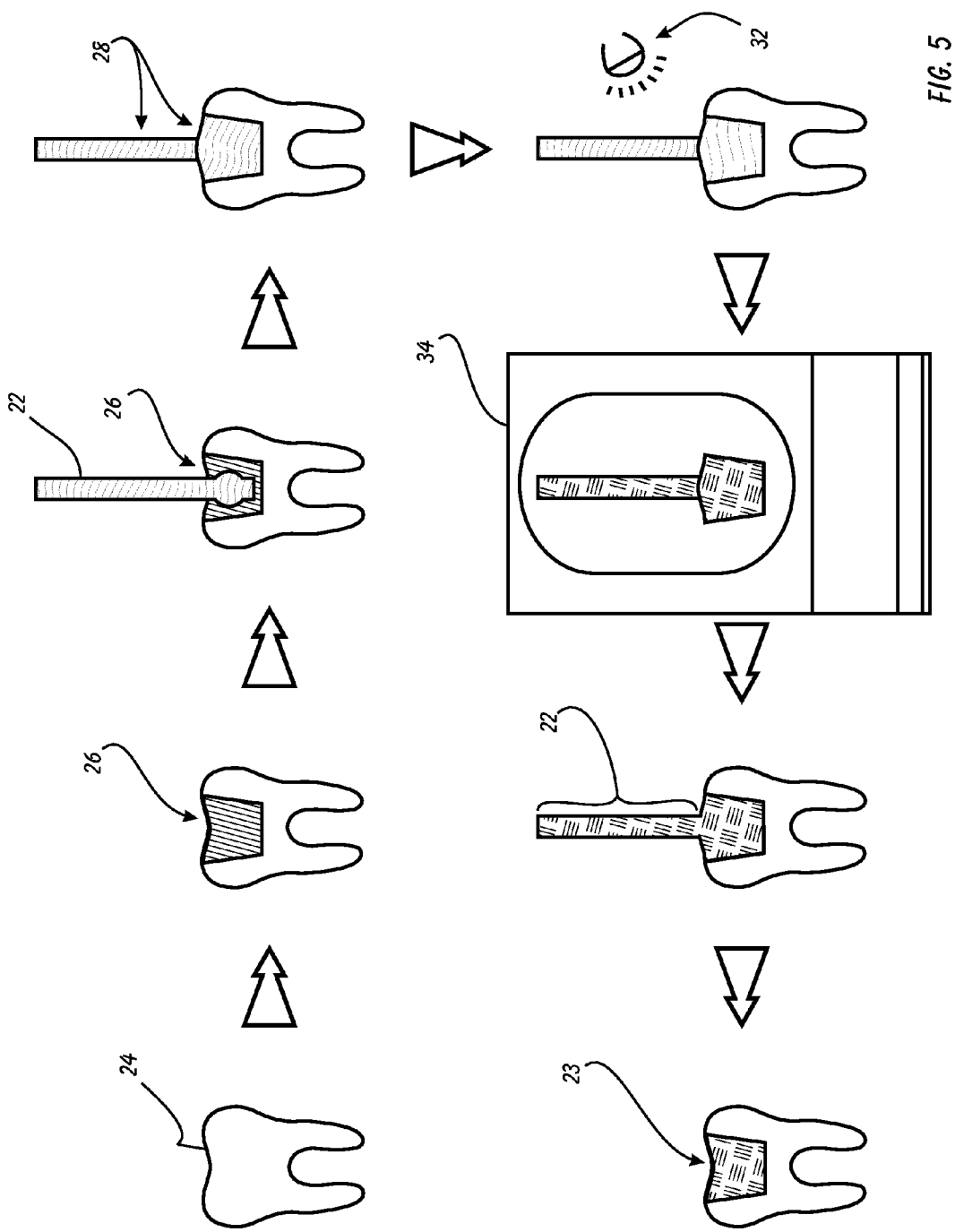
FIG. 5 depicts the method of FIG. 4 graphically.

Finally, the protruding portion of the filled/cured stem is cut off and the surface of the tooth (and excess filling material) is polished and shaped so that the patient has a comfortable bite and no interferences. FIG. 5 depicts this method in summary form pictorially.

In order to optimize the wide variety of tooth configurations and void shapes, a wide variety of shapes of stems 22 could be provided. A sample of these shapes and configurations are shown as elements 22A-22I in FIG. 6. The feature indicated in FIG. 22I is a pair of through-holes through that portion of the lower portion of the stem 22I. As discussed previously, the upper portion of the stems (generically 22) will protrude from the tooth until its removal at the end of the filling process. It is possible that grip features may be added to the outer surface of the upper portion of the stems 22 to aid the doctor and his or her staff in grasping the prosthetic/filling assembly [36] when removing it from the tooth, or otherwise handling it.

Those skilled in the art will appreciate that various adaptations and modifications of the just-described preferred embodiment can be configured without departing from the scope and spirit of the invention. Therefore, it is to be understood that, within the scope of the appended claims, the invention may be practiced other than as specifically described herein.

What is claimed is:

1. A method for repairing a tooth, comprising the steps of:
   creating a void in the tooth by removal of a portion of the tooth;
   inserting a first end of a hollow stem into said void;
   injecting filling material into said void by injecting said material in non-solid form into a second end of said hollow stem and out through said first end until said void is completely filled with said non-solid filling material;
   first curing said filling material in said stem and said void to form a partially cured prosthetic assembly;
   removing said partially cured prosthetic assembly from said tooth;
   second curing said prosthetic assembly; and re-inserting said prosthetic assembly into said void formed in said tooth.

2. The method of claim 1, further comprising:
a stem cutting step executed after said re-inserting step wherein the portion of said stem protruding from said prosthetic assembly is removed.

3. The method of claim 2, further comprising:
a shaping step, executed after said stem cutting step, wherein the shape of the exposed portion of said prosthetic assembly is adjusted to conform to the patient's other teeth.

4. The method of claim 3, further comprising an adhesive step between said removing step and said re-inserting step, said adhesive step comprising applying adhesive material between said prosthetic assembly and said void.

5. The method of claim 4, wherein the hollow stem used therein is made from substantially the same material as said filling material.

6. The method of claim 5, wherein said second curing step comprises exposing said prosthetic assembly to a pre-determined elevated temperature for a pre-determined period of time.

7. The method of claim 6, wherein said first curing step comprises exposing said filling material to light in a pre-selected wavelength for a pre-determined period of time.

8. The method of claim 7, wherein said injecting step is conducted in partial injections, with said first curing step being executed after each said partial injecting step, until the entire said void and stem are completely filled with said filling material and said filling material curing has been completed for all partial fills.

9. The method of claim 8, wherein said hollow stem comprises an elongate hollow tube that is further defined by an enlarged section along its length.

10. The method of claim 9, wherein said enlarged section is adjacent to said first end such that it is located within said void during said inserting and said injecting steps.

11. A method for installing a dental prosthetic into a void formed in a tooth, comprising the steps of:
inserting a first end of a hollow stem into said void;
injecting filling material into said void by injecting said material in non-solid form into a second end of said hollow stem and out through said first end until said void is completely filled with said non-solid filling material;
first curing said filling material to form a partially cured prosthetic assembly;
removing said partially cured prosthetic assembly from said void;
second curing said prosthetic assembly; and
re-inserting said prosthetic assembly into said void formed in said tooth.

12. The method of claim 11, further comprising an adhesive applying step between said removing step and said re-inserting step, said adhesive applying step comprising applying adhesive material between said prosthetic assembly and said void.

13. The method of claim 12, further comprising a stem cutting step executed after said re-inserting step wherein the portion of said stem protruding from said prosthetic assembly is removed.

14. The method of claim 13, further comprising a shaping step, executed after said stem cutting step, wherein the shape of the exposed portion of said prosthetic assembly is adjusted to conform to the patient's other teeth.

15. The method of claim 14, wherein the hollow stem used therein is made from substantially the same material as said filling material.

* * * * *